(12) United States Patent
Lin

(10) Patent No.: US 6,984,808 B2
(45) Date of Patent: Jan. 10, 2006

(54) HEAT GENERATOR

(75) Inventor: Jhy-Chain Lin, Tu-Cheng (TW)

(73) Assignee: Hon Hai Precision Industry Co., Ltd., (TW)

( * ) Notice: Subject to any disclaimer, the term of this patent is extended or adjusted under 35 U.S.C. 154(b) by 0 days.

(21) Appl. No.: 10/930,551

(22) Filed: Aug. 31, 2004

(65) Prior Publication Data

US 2005/0035107 A1    Feb. 17, 2005

(30) Foreign Application Priority Data

Mar. 12, 2003   (CN) .................... 200320119001 A

(51) Int. Cl.
    *H05B 1/02*  (2006.01)
    *H05B 3/28*  (2006.01)
    *G01N 25/18*  (2006.01)
    *F25B 21/02*  (2006.01)

(52) U.S. Cl. ................... 219/385; 219/201; 219/494; 374/44

(58) Field of Classification Search ........... 219/385, 219/386, 200, 201, 228, 494, 497; 374/44
See application file for complete search history.

(56) References Cited

U.S. PATENT DOCUMENTS

| | | | | |
|---|---|---|---|---|
| 3,114,255 A | * | 12/1963 | Niven | .................... 374/44 |
| 3,662,587 A | * | 5/1972 | Allen et al. | .................... 374/44 |
| 3,733,887 A | * | 5/1973 | Stanley et al. | ................. 374/44 |
| 4,929,089 A | | 5/1990 | Tsuchida | ...................... 374/44 |
| 5,258,929 A | * | 11/1993 | Tsuchida | ...................... 374/44 |
| 6,550,961 B1 | | 4/2003 | Ueda | ............................ 374/44 |
| 2003/0072349 A1 | | 4/2003 | Osone et al. | ................. 374/43 |

FOREIGN PATENT DOCUMENTS

DE     2724846 A   * 12/1978

* cited by examiner

*Primary Examiner*—Joseph Pelham
(74) *Attorney, Agent, or Firm*—Morris Manning & Martin; Tim Tingkang Xia, Esq.

(57) ABSTRACT

A heat generator includes a heat generating member for generating heat flow, a temperature compensating member, and a heat flow compensating circuit connected between the heat generating member and the temperature compensating member. The heat generating member includes a heat export face and a heat insulation face. The temperature compensating member includes a temperature compensating face facing the heat insulation face. The circuit is capable of controlling heat generated by a thermoelectric resistor of the temperature compensating member to cause the temperature of the temperature compensating face to be equal to the temperature of the heat insulation face, which results in the heat energy of the heat flow exporting out from the heat export face of the heat generating member to be substantially equal to the heat energy of the heat generated by the heat generating member.

11 Claims, 1 Drawing Sheet ically, the heat conductivity of a material is measured via sandwiching a specimen made of the material between a heat source and an object with a lower temperature. The heat generated by the heat source flows through the specimen to the object with lower temperature. A temperature gradient ΔT exists between two opposite ends of the specimen. The distance between the two opposite ends of the specimen ΔX can be measured. Assuming that all of the heat generated byte heat source flows through the specimen, the heat energy Q of the heat flow flowing through the specimen is equal to the heat energy Q' generated by the heat source. The heat energy Q' generated by the heat source is calculated according to the following equation:

$$Q'=\alpha I^2 R$$

wherein R is the resistance value of a thermoelectric resistor embedded in the heat source, I represents the electric current flowing through the thermoelectric resistor, and α is a ratio of electrical power converted to heat energy of the thermoelectric resistor. The heat conductivity K of the material of the specimen can be calculated according to the following equation:

$$K=q*\Delta X/\Delta T$$

wherein q represents heat flow, which is the rate at which heat energy Q flows through the specimen per square meter, measured in W/m².

In the above method, the specimen firmly contacts one face of the heat source. The other faces of the heat source are heat insulated by a layer of insulation material covered thereon in order to ensure all of the heat generated by the heat source flows through the specimen. However, the insulation capability of the insulation material, such as alumina, is limited. Some of the heat generated by the heat source is inevitably dissipated through the other faces which do not contact the specimen. That means, the measured heat energy Q of the heat flow flowing through the specimen is not equal to the actual heat energy Q' generated by the heat source. Because the value of the heat energy Q of the heat flow flowing through the specimen is defined to be equal to the value of the heat energy Q' generated by the heat source, the measured heat energy Q is inaccurate. This results in the calculated heat conductivity K of the material of the specimen being inaccurate.

SUMMARY OF THE INVENTION

Accordingly, an object of the present invention is to provide a heat generator which can export a predetermined heat flow precisely.

To achieve the above-mentioned object, a heat generator in accordance with the present invention comprises a heat generating member for generating heat, a temperature compensating member, and a temperature compensating circuit connected between the heat generating member and the temperature compensating member. The heat generating member comprises a heat export face and a heat insulation face. The temperature compensating member comprises a temperature compensating face facing the heat insulation face. The circuit is capable of controlling heat energy generated by a thermoelectric resistor of the temperature compensating member to cause the temperature of the temperature compensating face to be equal to the temperature of the heat insulation face which results in the heat energy of the heat flow exporting out from the heat export face of the heat generating member substantially being equal to the heat energy generated by the heat generating member.

Other objects, advantages and novel features of the present invention will be drawn from the following detailed description of a preferred embodiment of the present invention with attached drawings, in which:

DETAIL DESCRIPTION OF A PREFERRED EMBODIMENT

Figure 1:
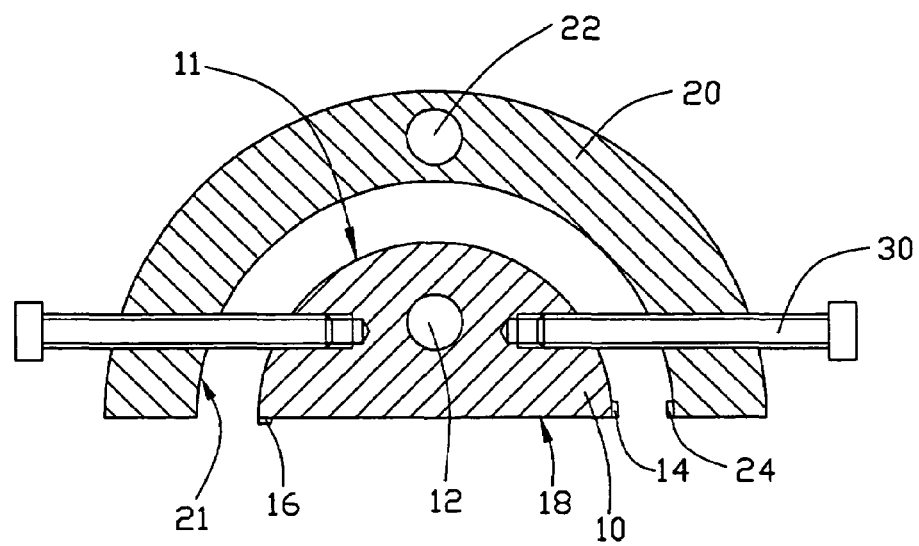
FIG. 1 is a cross-sectional view of a heat generator in accordance with a preferred embodiment of the present invention.

Referring to FIG. 1, a heat generator in accordance with the preferred embodiment of the present invention comprises a heat generating member 10 and a thermoelectric temperature compensating member 20.

The heat generating member 10 has a solid semi-spherical shape and comprises an outer semi-spherical face 11 and a planar bottom face 18. Each of the outer semi-spherical face 11 and the planar bottom face 18 has a layer of gold mounted thereon by plating for enabling the outer semi-spherical face 11 and the planar bottom face 18 to have a uniform temperature. A thermoelectric resistor 12 is embedded in the heat generating member 10 for generating a predetermined heat flow. The heat energy Q' generated by the thermoelectric resistor 12 is calculated according to the following equation:

$$Q'=\alpha I^2 R$$

wherein R is the resistance value of the thermoelectric resistor 12, I represents the electric current flowing through the thermoelectric resistor 12, and α is a ratio of electrical power converted to heat energy. A thermistor 14 is installed on the outer semi-spherical face 11 of the heat generating member 10 for sensing the temperatuare T14 of the outer semi-spherical face 11. A thermistor 16 is installed on the planar bottom face 18 of the heat generating member 10 for sensing the temperatuare of the planar bottom face 18.

The thermoelectric temperature compensating member 20 is a hollow semi-sphere receiving the heat generating member 10 therein. The thermoelectric temperature compensating member 20 comprises an inner semi-spherical face 21 having a same curvature with the outer semi-spherical face 11 of the heat generating member 10. The inner semi-spherical face 21 faces the outer semi-spherical face 11 of the heat generating member 10 with a small gap about 100 um formed therebetween. The thermoelectric temperature compensating member 20 is fixed to the heat generating member 10 by a plurality of screws 30 made of heat insulating material. The thermoelectric temperature compensating member 20 works based on the peltier effect which relates to a change in temperature at the junction of two different metals produced when an electric current flows through them. A thermoelectric resistor 22 is embedded in the thermoelectric temperature compensating member 20 for generating an adjustable heat flow. A thermistor 24 is installed on the inner semi-spherical face 21 of the thermoelectric temperature compensating member 20 for sensing the temperature T24 of the inner semi-spherical face 21.

Figure 2:
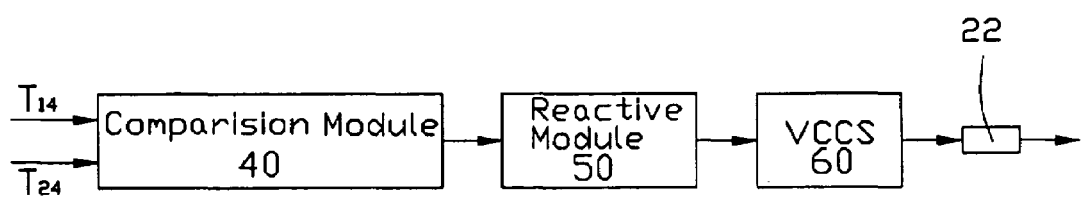
FIG. 2 is a diagram showing the heat flow compensating circuit of the heat generator.

Referring to FIG. 2, a heat flow compensating circuit is connected between the thermistor 14, the thermistor 24 and the thermoelectric resistor 22. The circuit comprises a comparision module 40, a reactive module 50 and a voltage control current source (VCCS) 60. The module 40 is used to compare the temperature T14, T24 of the heat generating member 10 and thermoelectric temperature compensating member 20. If the temperature T14 is not equal to the temperature T24 the module 40 outputs a voltage signal to the reactive module 50. The reactive module 50 outputs a reactive control signal to the VCCS 60. Accordingly, the VCCS 60 outputs an adjusted electric current to the thermoelectric resistor 22 thereby adjusting the heat generated by the thermoelectric resistor 22 to cause the temperature T24 of the inner semi-spherical face 21 of the thermoelectric temperature compensating member 20 to be equal to the temperature T14 of the outer semi-spherical face 11 of the heat generating member 10. Thus, no heat flow flows through the outer semi-spherical face 11 of the heat generating member 10 and the inner semi-spherical face 21 of the thermoelectric temperature compensating member 20 and all of the heat generated by the heat generating member 10 flow through the planar bottom face 18 of the heat generating member 10 to a specimen (not shown) which is an object of detecting heat conductivity. Therefore, the heat energy Q of the heat flow flowing through the specimen is equal to the heat energy Q' generated by the heat generating member 10.

In the present invention, no heat flow flows through the outer semi-spherical face 11 of the heat generating member 10 and the inner semi-spherical face 21 of the thermoelectric temperature compensating member 20, and all of the heat generated by the heat generating member 10 flows through the planar bottom face 18 of the heat generating member 10 to the specimen. So, the planar bottom face 18 of the heat generating member 10 is also called a heat flow export face, while the outer semi-spherical face 11 of the heat generating member 10 is called a heat insulation face. The inner semi-spherical face 21 of the thermoelectric temperature compensating member 20 is called a temperature compensating face.

It is understood that the invention may be embodied in other forms without departing from the spirit thereof. Thus, the present example and embodiment is to be considered in all respects as illustrative and not restrictive, and the invention is not to be limited to the details given herein.

What is claimed is:

1. A heat generator comprising:
   a heat generating member for generating heat, comprising a heat flow export face and a heat insulation face;
   a temperature compensating member having a temperature compensating face surrounding and facing the heat insulation face; and
   means for maintaining the temperature of the temperature compensating face to be equal to the temperature of the heat insulation face to thereby cause the heat energy of heat flow exporting out from the heat export face of the heat generating member to be equal to the heat energy of the heat generated by the heat generating member.

2. The heat generator as claimed in claim 1, wherein the maintaining means comprises a heat flow compensating circuit which comprises a comparison module which is capable of comparing the temperature of the heat insulation face and the temperature of the temperature compensating face, a reactive module, and a voltage control current source, the reactive module being capable of outputting a voltage signal to the voltage control current source when the temperatures of the temperature compensating face and the heat insulation face are not equal to each other.

3. The heat generator as claimed in claim 2, wherein the temperature compensating member has a thermoelectric resistor, and when the voltage control current source receives the voltage signal, the voltage control current source is capable of outputting an adjusted electric current to the thermoelectric resistor thereby adjusting bass generated by the thermoelectric resistor to cause the temperature of the temperature compensating race of the temperature compensating member to be equal to the temperature of the heat insulation face of to heat generating member.

4. The heat generator as claimed in claim 3, further comprising a pair of thermistors respectively installed on the temperature compensating face and the heat insulation face for sensing the temperatures thereof.

5. The heat generator as claimed in claim 1, wherein a gap exists between the temperature compensating face and the heat insulation face.

6. The heat generator as claimed in claim 5, wherein to heat generating member has a solid semi-spherical shape and the temperature compensating member has a hollow semi-spherical shape.

7. A heat generator comprising:
   a heat generating member for generating heat flow, comprising a heat flow export face and a heat insulation face;
   a temperature compensating member having a temperature compensating face confronting and spaced from the heat insulation face; and
   a circuit connected between to heat generating member and the temperature compensating member, the circuit being capable of controlling heat generated by the temperature compensating member to cause no heat flow flowing between the temperature compensating face and the heat insulation face whereby the heat energy of the heat flow exporting out from the beat export face of the heat generating member is equal to the heat energy of the heat generated by the heat generating member.

8. The heat generator as claimed in claim 7, wherein the circuit comprises a comparison module which is capable of comparing the temperature of the heat insulation face and the temperature of the temperature compensating face, a reactive module and a voltage control current source, and the reactive module is capable of outputting a voltage signal to the voltage control current source when the temperatures of the temperature compensating face and the heat insulation face are not equal to each other.

9. A method to provide heat to an object, comprising:
providing a heat generating member for generating heat provided to an object;
providing a temperature compensating member to surround at least one face of said heat generating member except a preset face of said beat generating member confronting with said object; and
sensing temperature of said temperature compensating member and temperature of said at least one face of said heat generating member surrounded by said temperature compensating member; and
adjusting said temperature of said temperature compensating member so as to provide a heat transmission balance between said temperature compensating member and said surrounded at least one face of said beat generating member.

10. The method as claimed in claim 9, further comprising using a circuit to compare said sensed temperatures and generate an electrical current to active said temperature compensating member.

11. The method as claimed in claim 9, wherein said preset face of said heat generating member is planar and said at least one face of said heat generating member surrounded by said temperature compensating member is spherical.

* * * * *